United States Patent
Zaiser et al.

(10) Patent No.: US 6,647,982 B1
(45) Date of Patent: Nov. 18, 2003

(54) GAS FLOW DEVICE

(76) Inventors: LeNoir E. Zaiser, 550 Admiralty Parade West, Naples, FL (US) 34102; Kevin Confoy, 895 10th Ave. South, Naples, FL (US) 34103

(*) Notice: Subject to any disclaimer, the term of this patent is extended or adjusted under 35 U.S.C. 154(b) by 0 days.

(21) Appl. No.: 09/342,953

(22) Filed: Jun. 29, 1999

Related U.S. Application Data

(60) Provisional application No. 60/127,961, filed on Apr. 6, 1999, provisional application No. 60/124,704, filed on Mar. 15, 1999, provisional application No. 60/119,745, filed on Feb. 9, 1999, and provisional application No. 60/091,127, filed on Jun. 29, 1998.

(51) Int. Cl.[7] .......................... A61M 16/00; E16K 31/12
(52) U.S. Cl. ........................ 128/204.18; 128/205.24; 137/507
(58) Field of Search ............... 128/204.18, 205.24, 128/202.27, 204.25, 204.29, 204.24, 202.24, 201.21, 201.28, 203.21, 203.24, 205.22; 137/505.28, 507; 251/368

(56) References Cited

U.S. PATENT DOCUMENTS

| | | | | |
|---|---|---|---|---|
| 3,911,948 A | * | 10/1975 | Collins et al. | 137/505.11 |
| 4,008,716 A | * | 2/1977 | Amlong | 128/205.24 |
| 4,062,356 A | * | 12/1977 | Merrifield | 128/205.22 |
| 4,064,890 A | * | 12/1977 | Collins et al. | 137/505.11 |
| 4,172,468 A | * | 10/1979 | Ruus | 137/504 |
| 4,256,138 A | * | 3/1981 | Chapman | 137/505.42 |
| 4,363,424 A | * | 12/1982 | Holben et al. | 222/4 |
| 4,699,173 A | * | 10/1987 | Rohling | 137/614.2 |
| 5,368,022 A | * | 11/1994 | Wagner | 128/205.24 |
| 5,413,096 A | * | 5/1995 | Hart | 128/205.24 |
| 5,785,050 A | * | 7/1998 | Davidson et al. | 128/205.24 |
| 6,009,900 A | * | 1/2000 | Elgert et al. | 137/505 |
| 6,082,359 A | * | 7/2000 | Preston | 128/205.24 |
| 6,082,396 A | * | 7/2000 | Davidson | 137/505 |
| 6,137,417 A | * | 10/2000 | McDermott | 128/202.22 |
| 6,158,457 A | * | 12/2000 | Byrd et al. | 137/505.25 |
| 6,189,531 B1 | * | 2/2001 | Tatarek | 128/203.24 |
| 6,240,943 B1 | * | 6/2001 | Smith | 137/1 |
| 6,286,543 B1 | * | 9/2001 | Davidson | 137/505.25 |
| 6,321,779 B1 | * | 11/2001 | Miller et al. | 137/340 |
| 6,325,097 B1 | * | 12/2001 | Gallant et al. | 137/505 |
| 6,484,720 B1 | * | 11/2002 | Marquard, II et al. | 128/205.24 |

* cited by examiner

*Primary Examiner*—Weilun Lo
*Assistant Examiner*—Teena Mitchell
(74) *Attorney, Agent, or Firm*—Hamilton, Brook, Smith & Reynolds, P.C.

(57) ABSTRACT

A gas flow regulator includes a one-piece housing with an internally disposed flowmeter. The flowmeter is screwed into the housing. A fitting, such as a hose barb, extends through the housing and into the body of the flowmeter to secure the pieces together. Similarly, an inner core assembly can be separately fabricated, screwed into the housing and secured by fittings. This allows a full brass core for oxygen regulators.

46 Claims, 7 Drawing Sheets

GAS FLOW DEVICE

RELATED APPLICATIONS

This application claims priority to U.S. Provisional Application No. 60/091,127 filed on Jun. 29, 1998, U.S. Provisional Application No. 60/119,745 filed on Feb. 9, 1999, U.S. Provisional Application No. 60/124,704 filed on Mar. 15, 1999 and U.S. Provisional Application No. 60/127,961 filed on Apr. 6, 1999; the teachings of which are all incorporated herein by reference in their entirety.

BACKGROUND

Gas flow regulators are used to provide a medical gas, such as oxygen, to a patient from a source supply of the gas. The gas is normally stored in a cylinder or supply vessel under high pressure. The gas flow regulator reduces the high pressure (about 500–3000 psi) to a lower pressure (about 50 p.s.i.) and provides the gas at a metered flow rate, measured in liters/minute. It is desirable to manufacture gas flow regulators as a compact, light weight and smooth to the touch package. It is also desirable to color code the devices to indicate the gas being handled (e.g., green for oxygen) or the preference of the owner of the device.

In the prior art, compact gas flow regulators are generally constructed in either a one-piece or two-piece aluminum alloy housing. In one-piece regulators, a pressure reducing element and flow control subassembly is typically held into the housing using a c-clip or snap ring. In these devices, the c-clips do not offer adequate stability. In addition, the flow control knob is usually snapped into place and can, therefore, accidentally separate from the regulator.

In two-piece regulators, a pressure reducing element and a piston are disposed within the yoke housing and a flow control housing, having a flow control element therein, screws together with the yoke housing. Consequently, the two-piece regulators have a characteristic division line between the yoke housing and the flow control housing. The use of two pieces also results in additional cosmetic problems. For example, it can be difficult to uniformly color the two housings due to variations in anodizing the pieces. Although two-piece regulators have a less desirable cosmetic appearance than one-piece regulators, the threaded attachment provides certain durability advantages.

SUMMARY OF THE DISCLOSURE

In accordance with a preferred embodiment of the invention, a gas flow regulator combines the durability advantages of two-piece "screw together" regulators with the cosmetic advantages of one-piece "c-clip" regulators. In particular, internal components are fabricated with a thread over their major diameter and are screwed into a yoke body which is fabricated to have a threaded minor diameter. The internal components are further secured in place by a fitting.

This combination of parts yields a one-piece regulator with improved durability and stability. In addition, the flow control knob is connected to the flow control body in such a way that the knob cannot separate from the regulator during use.

The modular system also permits the use of internal components which are fabricated from a different material than the yoke body. As such, the yoke body can be made from aluminum and the internal components can be made from brass. The resulting regulator can thus realize the advantageous of each material.

In accordance with an embodiment of the invention, a gas flow device includes an outer body with an inner cavity formed therein. The inner cavity is bounded by an inner wall of the outer body, the inner wall having a first coupling feature. An inner element, such as a pressure reducing element or a flow meter assembly, is disposed in the inner cavity. The inner element has an external wall with a second coupling feature. The inner element is secured within the inner cavity by mating the first and second coupling features.

The first and second coupling features can be matable threads. In addition, a fitting extends through the outer body and engages with the inner element to further secure the inner element within the outer body.

In accordance with another embodiment of the invention, a medical gas flow device provides gas at a selected flow rate from a pressurized supply tank. The device includes an outer body of a first material for physically connecting to the supply tank.

An inner core assembly is disposed within the outer body. The inner core assembly has an inlet for interfacing with gas from the supply tank and an outlet for outputting the gas at the selected flow rate. The gas traverses a gas flow path formed from a second material through the inner core assembly from the inlet to the outlet. In a particular embodiment, the outer body and the inner element or core assembly are of different materials. Specifically, the outer body is made of aluminum and the inner element is substantially made of brass.

BRIEF DESCRIPTION OF THE DRAWINGS

The foregoing and other objects, features and advantages of the invention will be apparent from the following more particular description of embodiments of the gas flow device, as illustrated in the accompanying drawings in which like reference characters refer to the same parts throughout the different views. The drawings are not necessarily to scale, emphasis instead being placed upon illustrating the principles of the invention.

DETAILED DESCRIPTION

Figure 1:
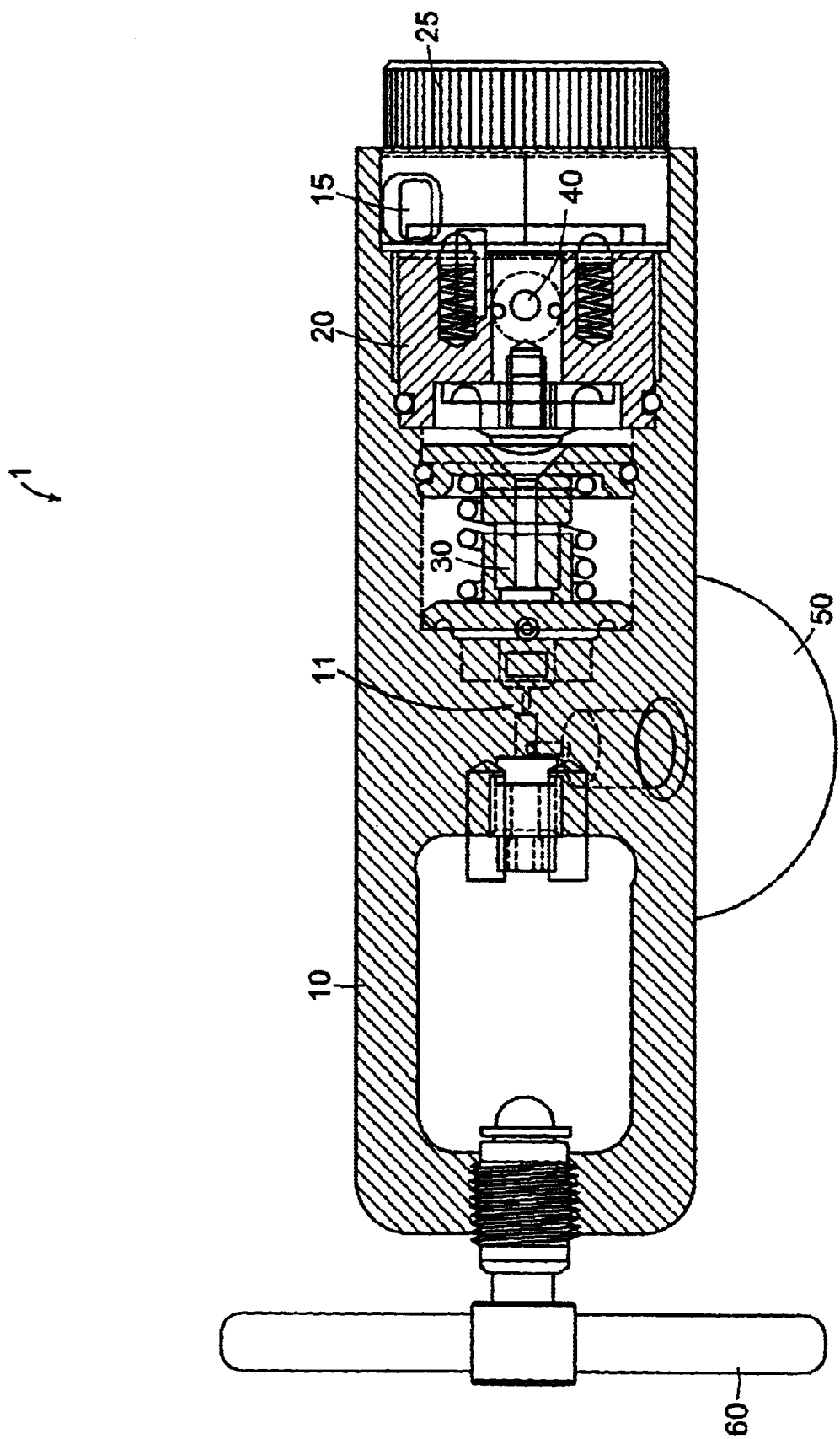
FIG. 1 is a cross-sectional diagram of a particular gas flow regulator.
Figure 2:
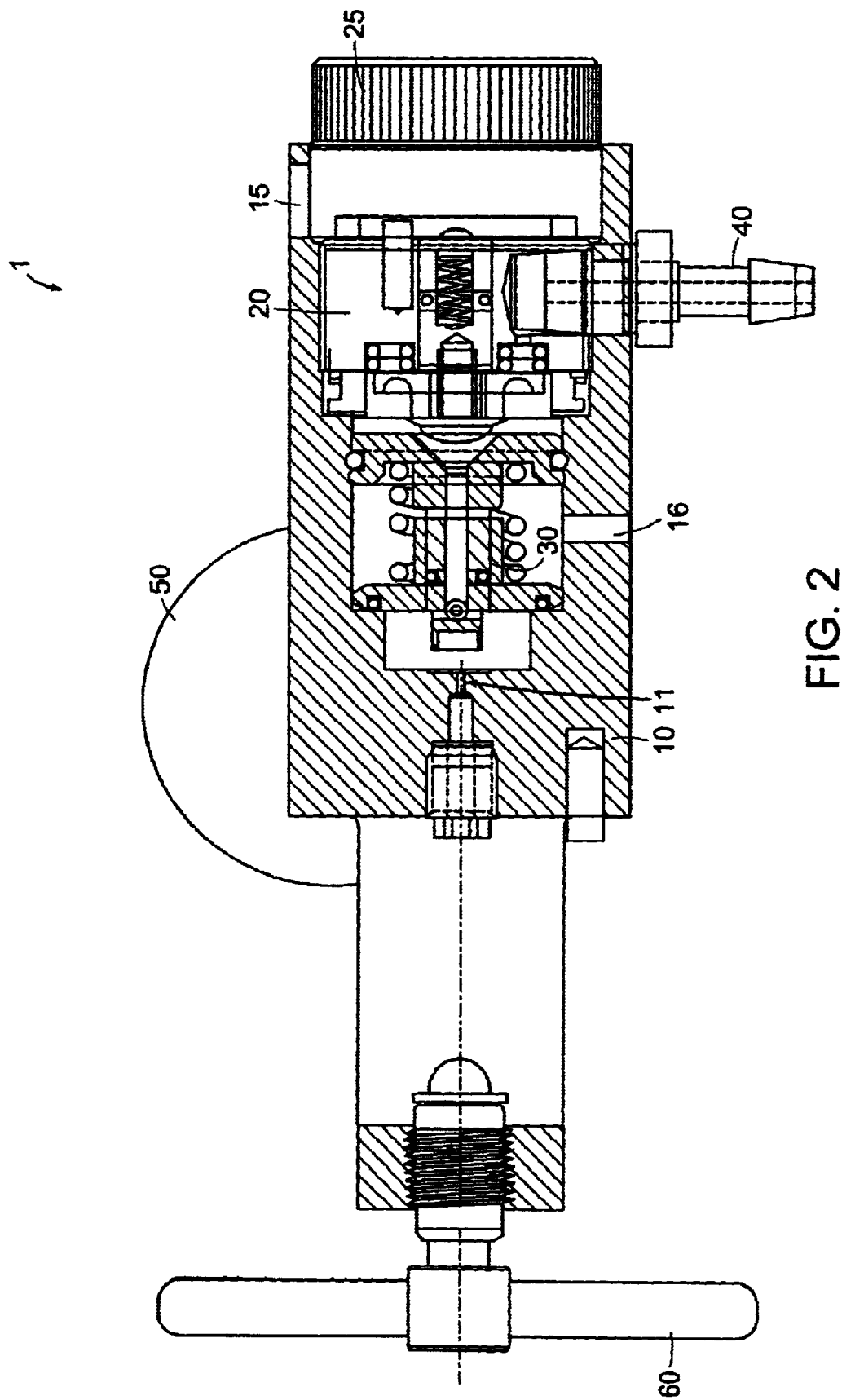
FIG. 2 is a cross-sectional diagram of the gas flow regulator of FIG. 1, rotated 90°.

FIGS. 1 and 2 are cross-sectional drawings of a particular gas flow regulator. The regulator 1 includes a yoke body or housing 10, a flowmeter assembly element 20, a piston element 30, a fitting such as a hose barb 40, a gauge 50 and a T-handle 60. The yoke body 10 is of a unibody construction to facilitate a secure and stable attachment to a gas supply cylinder (not shown). At a proximal end, the regulator is clamped to a cylinder or tank post of the supply cylinder by the handle 60. A pressure reducing region 11 of the yoke body 10 reduces the supply tank pressure to about 50 psi, as known in the art.

The piston 30 and flowmeter assembly 20 cooperate to supply the desired gas flow. The flowmeter 20 includes a control knob 25 for selection of a metered gas flow rate. A flowrate view window 15 through the yoke body 10 allows the user to view a selected flow rate registered to the setting (not shown) of the knob 25. Note that in FIG. 2 the flowrate view window 15 is shown rotated 45° from its true position to show details. The metered gas from the flowmeter 20 exits the regulator through the hose barb 40 at a distal end. A relief vent 16 extends through the yoke body 10 into the region of the piston 30 to vent high pressure gas in the event of a piston failure.

Figure 3:
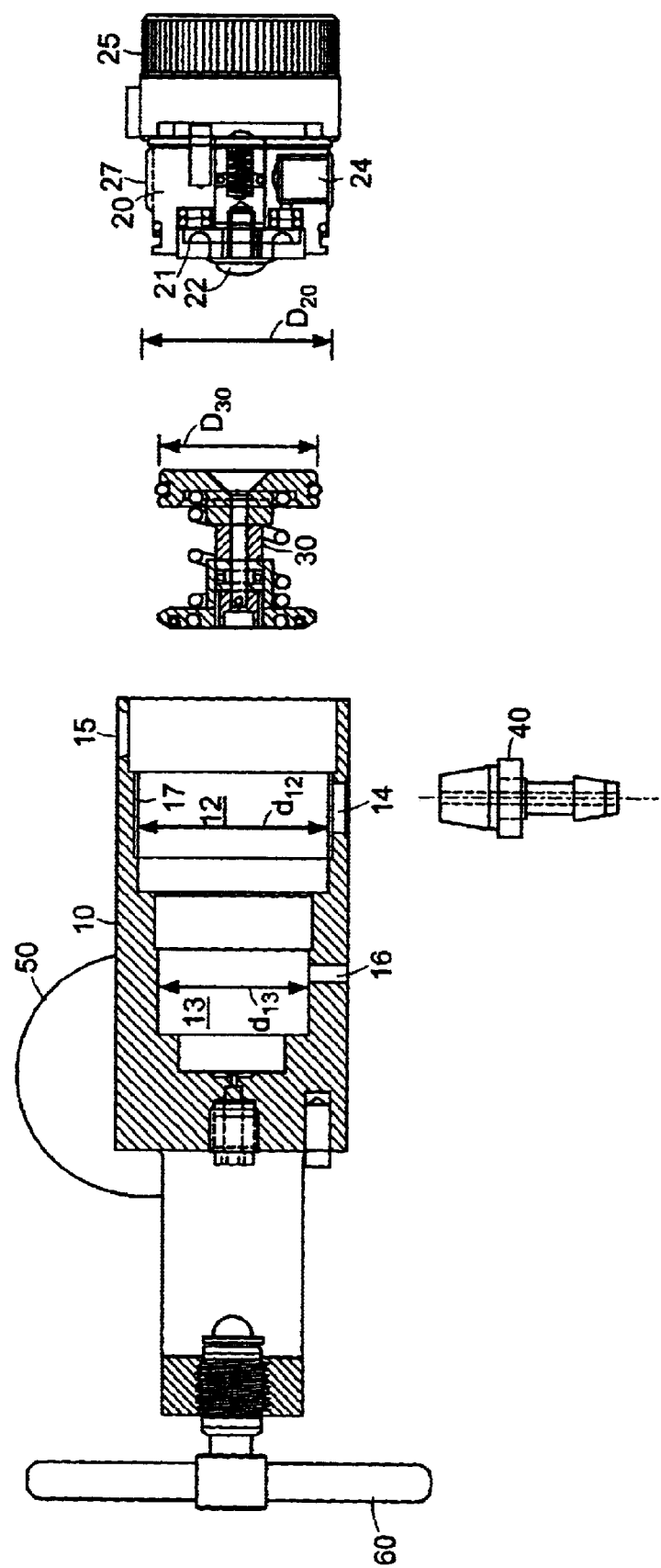
FIG. 3 is an exploded view, partially in cross-section, of the gas flow regulator of FIG. 2.

FIG. 3 is an exploded view, partially in cross section, of the gas flow regulator of FIG. 2. The piston 30 is received by a piston cavity 13 formed in the yoke body 10. Likewise, the flowmeter element 20 is received by a second cavity 12 in the yoke body 10. As illustrated, the flowmeter element 20 has a nominal major diameter $D_{20}$ which matches a nominal minor diameter $d_{12}$ of the flowmeter cavity 12. The piston 30 also has a major diameter $D_{30}$ which matches the minor diameter $d_{13}$ of the piston cavity 13.

The flow rate is determined by an orifice plate 21, which is attached to the knob 25 and thus the flowmeter element 20 by a retaining screw 22. Details of the orifice plate can be found in co-pending U.S. Ser. No. 08/941,356, entitled "Orifice Plate" by LeNoir E. Zaiser et al., the teachings of which are incorporated herein by reference in their entirety. As can be seen, the retaining screw 22 secures the knob 25 to the flowmeter element 20.

The flowmeter element 20 is, in turn, secured to the yoke body 10 by respective matable threads 27, 17 and the engagable barb 40. The threads 17, 27 are timed such that a barb port 24 in the flowmeter element 20 is center aligned with an output aperture 14 through the yoke body 10 and the flowrate view window 15 is aligned with flow rate numberings (not shown) on the knob 25 when the flowmeter element 20 is properly torqued into the yoke body 10. The yoke body 10 and flowmeter element 20 are locked in place by the barb 40, which is screwed through the output aperture 14 and into the barb port 24. This interlocking arrangement of parts using the threads 27 on the major diameter $D_{20}$ of the flowmeter body 20 yields a strong, durable and stable connection.

It should be understood that other output connectors, such as a DISS check valve, can be used in place of, or in addition to, the hose barb 40. It should also be understood that for clarity of description certain parts, such as O-rings and pins, are not illustrated. Although the piston cavity 13 and piston 30 are not shown as being threaded, threads may be included.

Because the exterior housing of the regulator can be a single piece, the regulator enjoys the cosmetic benefits of prior one-piece regulators, but in a more durable and stable package. For example, the one-piece yoke body 10 can be anodized or otherwise processed to a desired color. Consequently, the regulator can easily be manufactured to have a uniform color. In addition, the yoke body 10 can be laser etched.

In the embodiment shown in FIGS. 1–3, the pressure reducing region 11 is fabricated from the same material as the yoke body 10, namely an aluminum alloy. The piston 30 and the flowmeter 20 are fabricated from brass. It is currently believed that the use of aluminum in the flow path of oxygen, especially at high pressure, may contribute to a fire potential in medical oxygen regulators due to the relatively low burning point of aluminum.

One approach to remove aluminum from the gas flow path is to fabricate the main body of the regulator from brass or other suitable alloys. That brass main body can then be coupled to a stronger aluminum yoke. Unlike aluminum, however, brass cannot be anodized, which limits the manufacture's ability to color code the regulators. Perhaps more importantly, it may be more difficult to manufacture a suitably secure and rigid coupling. In addition, the increased amount of brass would increase the cost of the regulator without necessarily offering improved quality.

Figure 4:
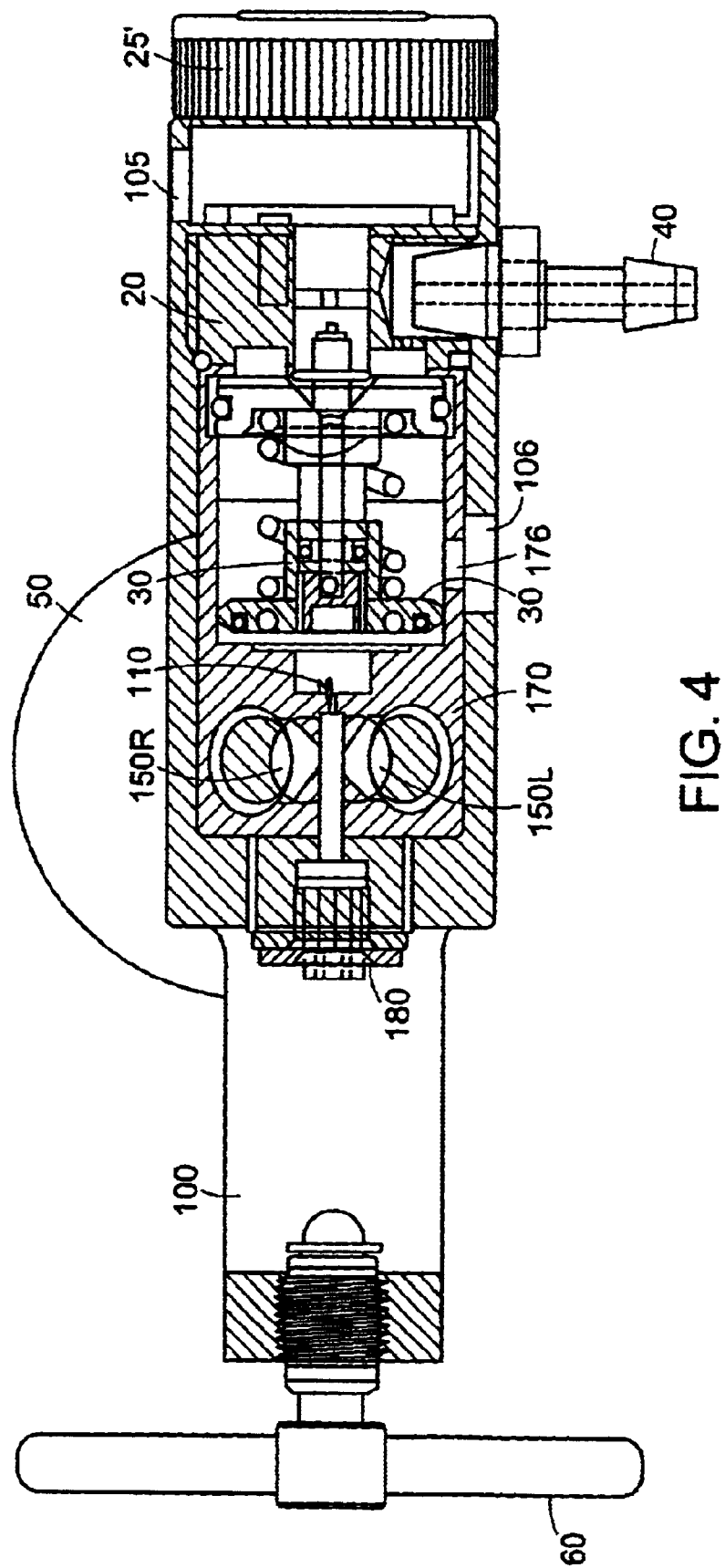
FIG. 4 is a cross-sectional diagram of a gas flow regulator with a full-core insert.

FIG. 4 is a cross-sectional diagram of a gas flow regulator with a full-core insert. As illustrated, the regulator is similar to the regulator of FIGS. 1–3, except that the yoke body 100 receives a pressure reduction element 170. The piston 30 resides inside a cavity of the pressure reduction element 170 defined by an extended wall 175. The flowmeter assembly 20 interfaces with the piston 30 within the cavity of the pressure reduction element 170. Also shown is a yoke inlet 180 for interfacing with the supply tank (not shown). A high pressure gauge port 150L, 150R for left or right-handed gauges is also shown.

As shown, the pressure reduction element 170 includes a vent hole 176. The yoke body 100 includes a vent window 106 having a larger diameter than the vent hole 176. As such, a user can see a section of the pressure reduction element 170 through the vent window 106 and can visually verify that the core is a suitable material such as brass. More importantly, in the event of a fire, the larger diameter vent window 106 in the aluminum yoke body 100 reduces the opportunity for any flames ejected from the piston area through the vent hole 176 to ignite the aluminum.

Figure 5:
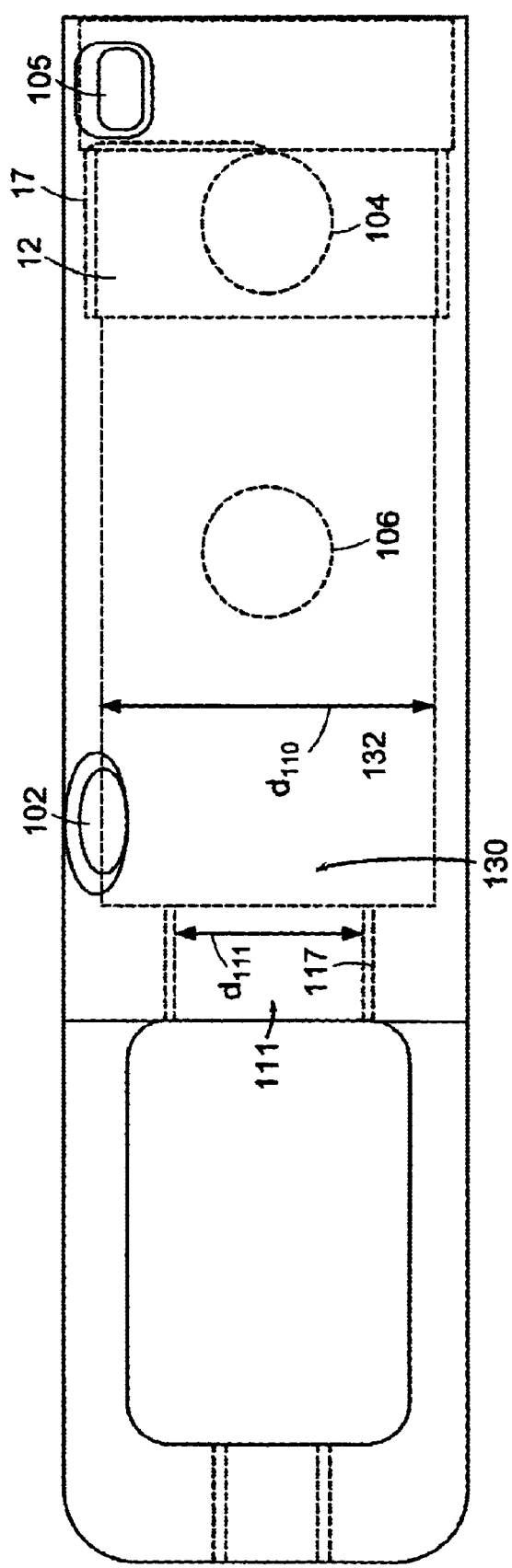
FIG. 5 is a diagram of the yoke body of FIG. 4 rotated 90°.

FIG. 5 is a diagram of the yoke body of FIG. 4 rotated 90°. Exterior features include a hose barb output aperture 104, a high pressure gauge aperture 102, a vent window 106, and a flowrate view window 105. Interior features include a main cavity 130 having a minor diameter $d_{130}$ for receiving the pressure reduction element 170 (FIG. 4). Threads 117 are formed at a neck region 111 of the main cavity 130. The neck cavity 111 has a minor diameter $d_{111}$.

Figure 6:
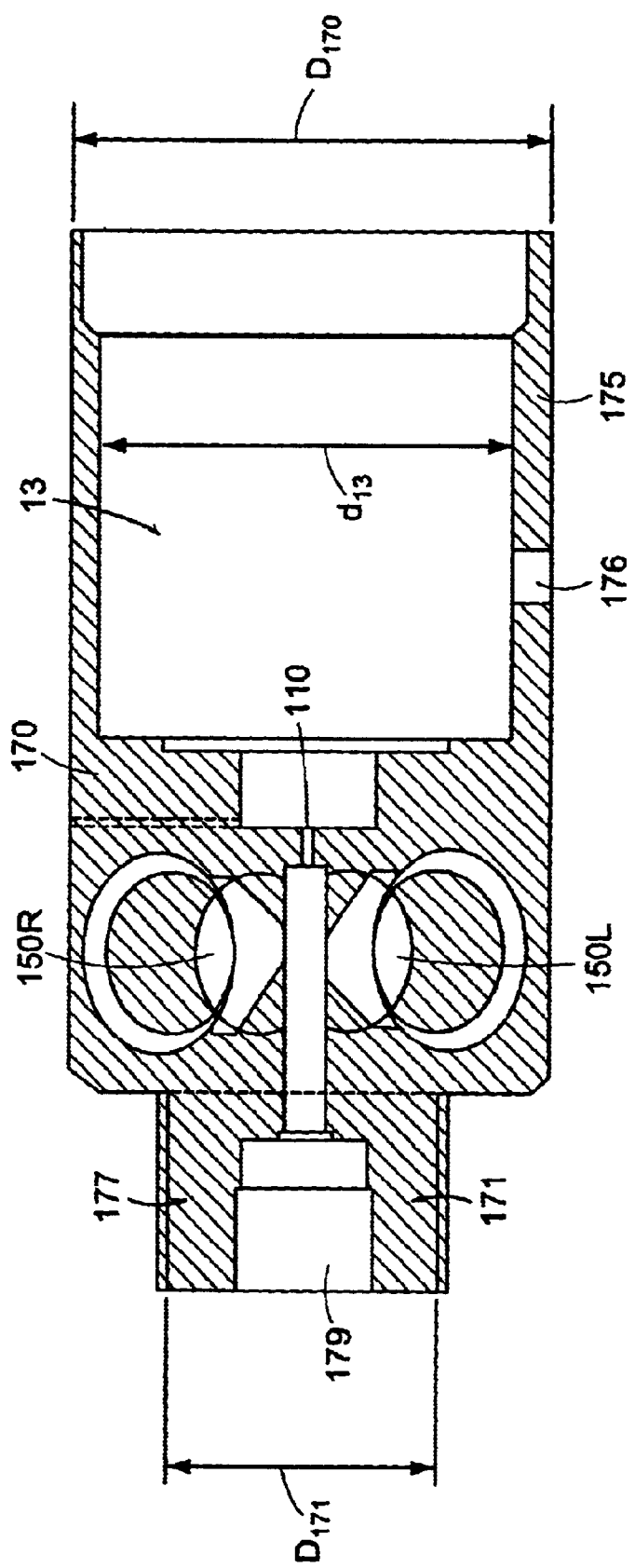
FIG. 6 is a cross-sectional diagram of the pressure reduction element of FIG. 4.

FIG. 6 is a cross-sectional diagram of the pressure reduction element of FIG. 4. The pressure reduction element 170 includes the pressure reducing features 110 for yielding a 50 psi internal pressure from the supply pressure. An inlet cavity 179 receives the inlet 180 (FIG. 4).

A neck portion 171 has a major diameter $d_{171}$ which matches the minor diameter $d_{111}$ of the neck cavity 111 (FIG. 5). Threads 177 on the neck 171 of the pressure reduction element 170 mate with the threads 117 (FIG. 5) of the yoke body 100. The body of the pressure reduction element 170 has a major diameter $D_{170}$ which matches the minor diameter $d_{130}$ of the main cavity 130 (FIG. 5). Note that the piston cavity 13 is now located within the pressure reduction element 170.

It should be recognized that the extended wall 175 can be further extended to receive the flowmeter assembly 20. For example, the wall 175 may extend to the output aperture 104 or to the flowrate view window 105 (FIG. 5). Such a configuration can be achieved by increasing the diameter $D_{170}$ of the pressure reduction element 170 and increasing the diameter $d_{130}$ of the main cavity 130 a suitable amount. Alternatively, the piston 30 may reside in a cavity defined by a wall of the flowmeter element 20 instead of the pressure reduction element 170. Such embodiments may reduce the need for certain O-rings, reducing the number of parts and simplifying assembly of the parts.

When assembled, the high pressure gauge 50 extends through the gauge aperture 102 and engages a gauge port 150L, 150R to help secure the pressure reduction element 170 in place. The threads 117, 177 are timed such that, when the pressure reduction element 170 is properly torqued, the gauge port 150 is concentrically aligned with the gauge aperture 102 and the vent hole 176 is concentrically aligned with the vent aperture 104, within allowed tolerances. Because the gauge 50 screws into the pressure reduction element 170, the high pressure gas flow directly from the pressure reduction element 170 to the gauge 50 without being exposed to the aluminum in the yoke body 100. In a particular embodiment, a Teflon shim at the neck 171 of the pressure reduction element 170 is used to further secure the pressure reduction element 170 without the yoke body 100.

Figure 7:
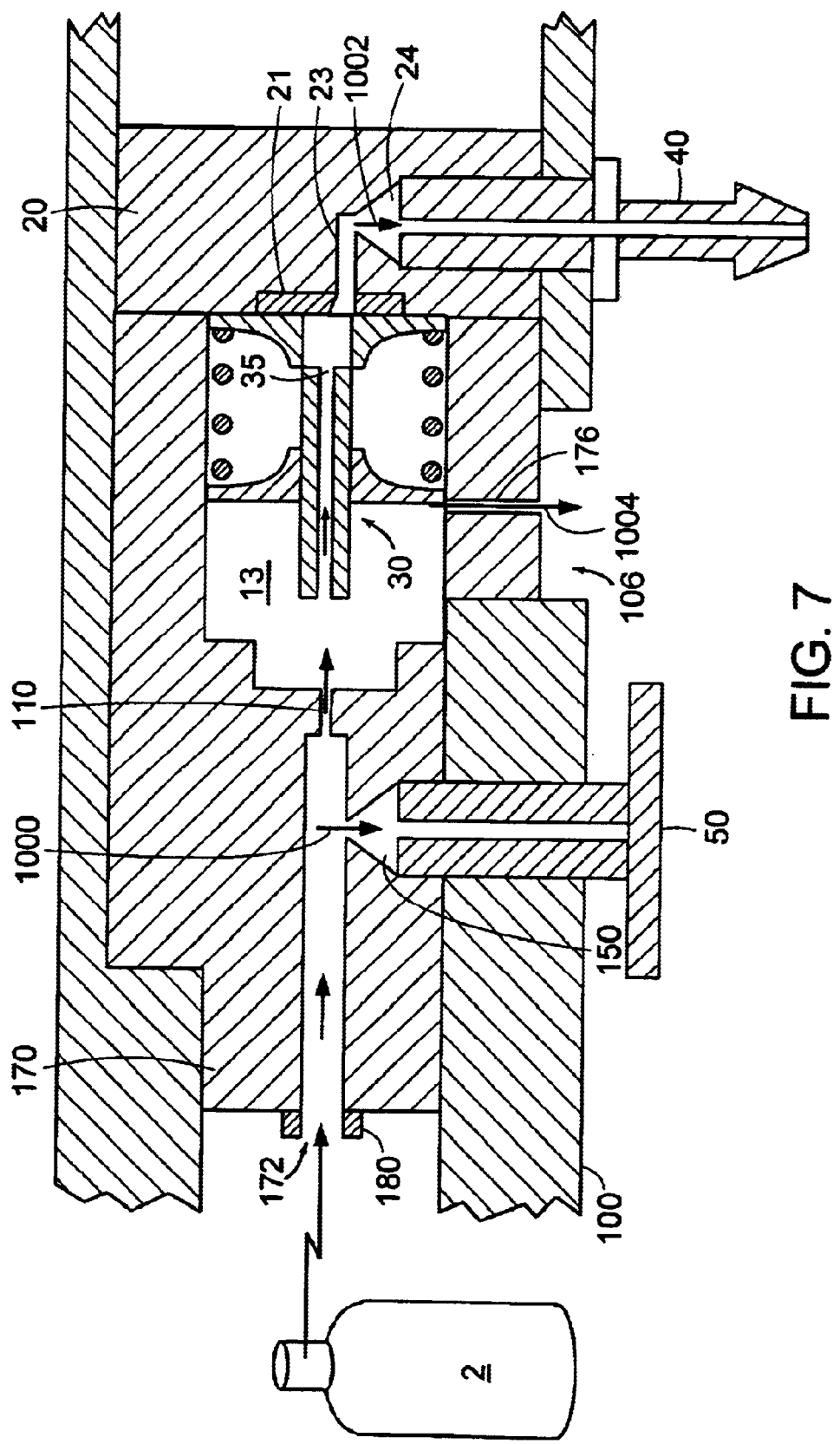
FIG. 7 is a schematic diagram of the primary gas flow paths through the regulator of FIG. 4.

FIG. 7 is a schematic cross-sectional diagram of the primary gas flow paths through the regulator of FIG. 4. High pressure gas from a supply tank 2 enters the regulator through the coupler 180 and flows along a high pressure passage 172 of the pressure reducing element 170 to the pressure reducing feature 110, which can be a smaller diameter passage dimensioned to provide a working pressure. The high pressure gas also flows into one or more high pressure ports 150, which are threaded to receive a pressure gauge 50 or other high pressure devices. This constitutes a normal high pressure flow path 1000. If the pressure reducing element is operating correctly, the gas pressure is reduced and flows into the piston chamber 13. The low pressure gas is maintained at the desired pressure by a piston assembly 30, which is shown compressed to its over-pressurize position.

Normally, the low pressure gas flows along a piston passage 35 of the piston assembly 30 and through the orifice plate 21, which determines the flow rate of the gas. After passing through the orifice plate 21, the gas flows through a flowmeter passage 23 and enters an output port 24 to which a barb 40 or other fitting (FIG. 3) is coupled to deliver the gas to the patient. This is the delivery flow path 1002.

In the event of an abnormal pressure buildup, such as resulting from a failure of the pressure reducing feature 110, high pressure gas can enter the piston chamber 13. To prevent this over-pressurized gas from being delivered along the delivery path 1002 to the patient, there is a vent 176 to the atmosphere. More particularly, as the pressure in the piston chamber increases, the piston assembly 30 compresses its spring until the piston chamber 13 is in communication with the vent 176 forming a vent pathway 1004. The corresponding opening 106 in the housing 100 is dimensioned to be outside the flow path.

Regulators embodying aspects of the invention are commercially available from Inovo, Inc. of Naples Fla. and distributed by various distributers, including Tri-anim of Sylmar, Calif. under the trademark Magnus.

While this invention has been particularly shown and described with references to embodiments thereof, it will be understood by those skilled in the art that various changes in form and details may be made therein without departing from the spirit and scope of the invention as defined by the appended claims.

For example, although the interior elements are shown and described as coupling with the exterior yoke body using matched and timed threads, other couplings may be used, including twist-lock couplings. In addition, the configuration required to couple the regulator to a gas supply source is defined by the Compressed Gas Association (CGA). The configuration described herein is for a CGA-870 tank connection, but the invention can be employed in other configuration including CGA-540 nut and nipple connections. Furthermore, aspects of the invention can be employed in other gas flow devices, such as pressure reducers.

What is claimed is:

1. A gas flow device for delivering a flow of medical oxygen at a prescribed dosage from a pressurized supply vessel to a patient, comprising:
   an outer body formed from a unitary piece of a first material, the first material having a first burning point in the presence of pressured pure oxygen, the outer body having an integrated yoke matable to a pressurized supply vessel and an inner cavity formed in the outer body, the outer body and the inner cavity bounded by an inner wall of the outer body;
   an inner core having a pressure reducing element and an oxygen flow path from the pressured supply vessel through the pressure reducing element, the flow path bounded by a second material, the second material having a second burning point in the presence of pressurized pure oxygen that is higher than the first burning point, the inner core substantially enclosed within the inner cavity; and
   a securing mechanism to secure the inner core within the outer body.

2. The gas flow device of claim 1 wherein the securing mechanism includes a member that locks the inner core within the outer body.

3. The gas flow device of claim 2 wherein the member is a fitting.

4. The gas flow device of claim 2 wherein the fitting is a pressure gauge.

5. The gas flow device of claim 2 wherein the fitting is a check valve.

6. The gas flow device of claim 1 wherein the first material comprises aluminum and the second material comprises brass.

7. The gas flow device of claim 1 wherein the securing mechanism includes a coupling for attaching the inner core to the inner wall of the outer body.

8. The device of claim 1 wherein the pressurized oxygen is over about 500 pounds per square inch.

9. The device of claim 1 wherein the pressurized oxygen is over about 50 pounds per square inch.

10. The device of claim 1 wherein the pressurized oxygen is between about 25–10,000 pounds per square inch.

11. A gas flow device for delivering oxygen at a selected flow rate from a pressured supply vessel, the device comprising:
    an outer body of a first material, the first material being ignitable when exposed to high pressure oxygen;
    a yoke for mounting the outer body to a supply vessel having pressurized oxygen stored therein; and
    an inner core assembly substantially enclosed by the outer body, the inner core assembly having an inlet for interfacing with the pressurized oxygen from the supply vessel, an outlet for outputting the oxygen at the selected flow rate and a vent between the inlet and outlet for discharging over-pressurized oxygen, the oxygen traversing a flow path bounded by a second material through the inner core assembly from the inlet to the vent, the second material resistant to ignition when exposed to high pressure oxygen.

12. The device of claim 11 wherein the second material excludes aluminum.

13. The device of claim 12 wherein the second material is brass.

14. The device of claim 11 wherein the inner core is positioned within the outer body by a coupling feature.

15. The device of claim 14 wherein the coupling feature includes matable threads.

16. The device of claim 11 further comprising a locking member engaging the outer body and the inner core to secure the inner core within the outer body.

17. The device of claim 11 wherein the first material and the second material are metal alloys.

18. The device of claim 11 wherein the high pressure oxygen is over about 50 pounds per square inch.

19. The device of claim 11 wherein the high pressure oxygen is over about 500 pounds per square inch.

20. The device of claim 11 wherein the high pressure oxygen is over about 25–10,000 pounds per square inch.

21. A method of fabricating a gas flow device for delivering oxygen at a selected flow rate from a pressurized supply vessel, the method comprising:

forming an outer body of a first material, the first material ignitable when exposed to high pressure oxygen;

providing a yoke for securing the outer body to a supply vessel having pressurized oxygen stored therein;

assembling an inner core assembly, the inner core assembly having an inlet for interfacing with the pressurized oxygen from the supply vessel, an outlet for outputting the oxygen at the selected flow rate, and a vent disposed between the inlet and the outlet for discharging over-pressurized oxygen, the oxygen traversing a flow path bounded by a second material through the inner core assembly from the inlet to the vent, wherein the second material inhibits ignition when exposed to high pressure oxygen; and substantially enclosing the inner core assembly within the outer body.

22. The method of claim 21 wherein the second material excludes aluminum.

23. The method of claim 22 wherein the second material is brass.

24. The method of claim 21 further comprising positioning the inner core within the outer body by a coupling feature.

25. The method of claim 24 wherein the coupling feature includes matable threads.

26. The method of claim 21 further comprising engaging the outer body and the inner core with a locking member to secure the inner core within the outer body.

27. The method of claim 21 wherein the first material and the second material are metal alloys.

28. The method of claim 21 wherein the high pressure oxygen is over about 50 pounds per square inch.

29. The method of claim 21 wherein the high pressure oxygen is over about 500 pounds per square inch.

30. The method of claim 21 wherein the high pressure oxygen is over about 25–10,000 pounds per square inch.

31. The method of claim 21 wherein the first material is a metal alloys.

32. A gas flow device for delivering a flow of medical oxygen at a prescribed dosage from a pressurized supply vessel to a patient, comprising:

an outer body formed from a unitary piece of a first material, the first material comprises aluminum having a first burning point in the presence of pressured pure oxygen, the outer body having an integrated yoke matable to a pressurized supply vessel and an inner cavity formed in the outer body, the outer body and the inner cavity bounded by an inner wall of the outer body;

an inner core having a pressure reducing element and an oxygen flow path from the pressured supply vessel through the pressure reducing element, the flow path bounded by a second material, the second material comprises brass having a second burning point in the presence of pressurized pure oxygen that is higher than the first burning point, the inner core substantially enclosed within the inner cavity; and a securing mechanism to secure the inner core within the outer body.

33. The gas flow device of claim 32 wherein the securing mechanism includes a member that locks the inner core within the outer body.

34. The gas flow device of claim 33 wherein the member is a fitting.

35. The gas flow device of claim 33 wherein the fitting is a pressure gauge.

36. The gas flow device of claim 33 wherein the fitting is a check valve.

37. The gas flow device of claim 32 wherein the securing mechanism includes a coupling for attaching the inner core to the inner wall of the outer body.

38. A gas flow device for delivering oxygen at a selected flow rate from a pressured supply vessel, the device comprising:

an outer body of a first material, the first material being ignitable when exposed to high pressure oxygen;

a yoke for mounting the outer body to a supply vessel having pressurized oxygen stored therein; and an inner core assembly substantially enclosed by the outer body, the inner core assembly having an inlet for interfacing with the pressurized oxygen from the supply vessel, an outlet for outputting the oxygen at the selected flow rate and a vent between the inlet and outlet for discharging over-pressurized oxygen, the oxygen traversing a flow path bounded by a second material through the inner core assembly from the inlet to the vent, the second material comprises brass that is resistant to ignition when exposed to high pressure oxygen.

39. The device of claim 38 wherein the inner core is positioned within the outer body by a coupling feature.

40. The device of claim 39 wherein the coupling feature includes matable threads.

41. The device of claim 38 further comprising a locking member engaging the outer body and the inner core to secure the inner core within the outer body.

42. The device of claim 38 wherein the first material is a metal alloy.

43. A method of fabricating a gas flow device for delivering oxygen at a selected flow rate from a pressurized supply vessel, the method comprising:

forming an outer body of a first material, the first material ignitable when exposed to high pressure oxygen;

providing a yoke for securing the outer body to a supply vessel having pressurized oxygen stored therein;

assembling an inner core assembly, the inner core assembly having an inlet for interfacing with the pressurized oxygen from the supply vessel, an outlet for outputting the oxygen at the selected flow rate, and a vent disposed between the inlet and the outlet for discharging over-pressurized oxygen, the oxygen traversing a flow path bounded by a second material through the inner core assembly from the inlet to the vent, wherein the second material comprises brass that inhibits ignition when exposed to high pressure oxygen; and substantially enclosing the inner core assembly within the outer body.

44. The method of claim 43 further comprising positioning the inner core within the outer body by a coupling feature.

45. The method of claim 44 wherein the coupling feature includes matable threads.

46. The method of claim 43 further comprising engaging the outer body and the inner core with a locking member to secure the inner core within the outer body.

* * * * *